US009138430B2

(12) United States Patent
Neely et al.

(10) Patent No.: US 9,138,430 B2
(45) Date of Patent: Sep. 22, 2015

(54) FORMULATION AND METHOD FOR THE RELEASE OF PAROXETINE IN THE LARGE INTESTINE

(75) Inventors: Jason Neely, Morgantown, WV (US); David J. Wargo, Pittsburgh, PA (US); Boyong Li, Morgantown, WV (US); Thomas D. Reynolds, Morgantown, WV (US)

(73) Assignee: Mylan Specialty L.P., Basking Ridge, NJ (US)

( * ) Notice: Subject to any disclaimer, the term of this patent is extended or adjusted under 35 U.S.C. 154(b) by 111 days.

(21) Appl. No.: 11/965,375

(22) Filed: Dec. 27, 2007

(65) Prior Publication Data

US 2009/0169616 A1 Jul. 2, 2009

(51) Int. Cl.
| | |
|---|---|
| *A61K 31/4525* | (2006.01) |
| *A61K 9/22* | (2006.01) |
| *A61K 9/52* | (2006.01) |
| *A61P 25/24* | (2006.01) |
| *A61P 25/00* | (2006.01) |
| *A61K 9/28* | (2006.01) |

(52) U.S. Cl.
CPC ........... *A61K 31/4525* (2013.01); *A61K 9/2846* (2013.01)

(58) Field of Classification Search
None
See application file for complete search history.

(56) References Cited

U.S. PATENT DOCUMENTS

| | | | |
|---|---|---|---|
| 3,912,743 A | 10/1975 | Christensen et al. | |
| 4,007,196 A | 2/1977 | Christensen et al. | |
| 4,590,213 A | 5/1986 | Stark | |
| 4,623,728 A | 11/1986 | Sarges | |
| 4,721,723 A | 1/1988 | Barnes et al. | |
| 4,775,536 A | 10/1988 | Patell | |
| 4,839,177 A | 6/1989 | Colombo et al. | |
| 4,933,186 A | 6/1990 | Ohm et al. | |
| 4,971,998 A | 11/1990 | Wurtman et al. | |
| 5,114,976 A | 5/1992 | Norden | |
| 5,171,580 A | 12/1992 | Iamartino et al. | |
| 5,258,517 A | 11/1993 | Zepp et al. | |
| 5,283,263 A | 2/1994 | Norden | |
| 5,422,123 A | 6/1995 | Conte et al. | |
| 5,425,950 A | 6/1995 | Dandiker et al. | |
| 5,540,945 A | 7/1996 | Ikushima | |
| 5,589,512 A | 12/1996 | Norden | |
| 5,661,162 A | 8/1997 | MacLeod et al. | |
| 5,672,612 A | 9/1997 | Ronsen et al. | |
| 5,744,501 A | 4/1998 | Norden | |
| 5,789,449 A | 8/1998 | Norden | |
| 5,856,493 A | 1/1999 | Ward et al. | |
| 5,872,132 A | 2/1999 | Ward et al. | |
| 5,874,447 A | 2/1999 | Benneker et al. | |
| 5,900,423 A | 5/1999 | Ward et al. | |
| 5,955,475 A | 9/1999 | Krape et al. | |
| 5,962,689 A | 10/1999 | Murthy et al. | |
| 6,027,748 A | 2/2000 | Conte et al. | |
| 6,080,759 A | 6/2000 | Ward et al. | |
| 6,113,944 A | 9/2000 | Pathak et al. | |
| 6,121,291 A | 9/2000 | Gleason | |
| 6,133,289 A | 10/2000 | Ward et al. | |
| 6,168,805 B1 | 1/2001 | Hein, II et al. | |
| 6,172,233 B1 | 1/2001 | Ward | |
| 6,326,496 B1 | 12/2001 | Brennan | |
| 6,433,179 B1 | 8/2002 | Wang et al. | |
| 6,436,956 B1 | 8/2002 | Murthy et al. | |
| 6,440,459 B1 | 8/2002 | Stampa Diez del Corral et al. | |
| 6,476,227 B1 | 11/2002 | Sugi et al. | |
| 6,503,927 B1 | 1/2003 | Ronsen et al. | |
| 6,541,637 B1 | 4/2003 | Okatake et al. | |
| 6,548,084 B2 | 4/2003 | Leonard et al. | |
| 6,583,287 B1 | 6/2003 | Rossi et al. | |
| 6,596,309 B2 | 7/2003 | Einig et al. | |
| 6,610,851 B1 | 8/2003 | Sugi et al. | |
| 6,638,948 B1 | 10/2003 | Ronsen et al. | |
| 6,645,523 B2 | 11/2003 | Lemmens et al. | |
| 6,645,528 B1 | 11/2003 | Straub et al. | |
| 6,657,062 B1 | 12/2003 | Kreidl et al. | |
| 6,660,298 B1 | 12/2003 | Ronsen et al. | |
| 6,686,473 B2 | 2/2004 | Lemmens et al. | |
| 6,699,882 B2 | 3/2004 | Craig et al. | |

(Continued)

FOREIGN PATENT DOCUMENTS

| | | | |
|---|---|---|---|
| WO | WO 92/09281 | 6/1992 | |
| WO | WO 2006/123364 | * 11/2006 | .............. A61P 25/24 |

OTHER PUBLICATIONS

Li et al, 2004. Enteric-coated layered double hydroxides as a controlled release drug delivery system. International Journal of Pharmaceutics, vol. 287:89-95.*

(Continued)

*Primary Examiner* — Patricia A Duffy
*Assistant Examiner* — Garen Gotfredson
(74) *Attorney, Agent, or Firm* — Timothy Balts (Alston & Bird)

(57) ABSTRACT

The present invention provides a delayed and/or controlled release formulation of paroxetine or a pharmaceutically acceptable salt thereof that is formulated to release a substantial portion of the active ingredient (e.g., paroxetine) in the large intestine of an individual in need thereof. In one embodiment, the present invention provides a controlled release paroxetine composition comprising paroxetine or a pharmaceutically acceptable salt thereof, in a controlled release swallow pharmaceutical formulation, that upon administration, releases the paroxetine substantially in the large intestine. For example, the controlled release paroxetine formulation may be formulated to release greater than about 50% of the paroxetine in the large intestine.

21 Claims, 4 Drawing Sheets

(56) References Cited

U.S. PATENT DOCUMENTS

| | | | |
|---|---|---|---|
| 6,703,408 | B2 | 3/2004 | Hoorn et al. |
| 6,716,985 | B2 | 4/2004 | Jacewicz et al. |
| 6,777,554 | B2 | 8/2004 | Finkelstein |
| 6,815,548 | B2 | 11/2004 | Sugi et al. |
| 6,833,458 | B2 | 12/2004 | Liu et al. |
| 6,900,327 | B2 | 5/2005 | Benneker et al. |
| 6,929,803 | B2 | 8/2005 | Wong et al. |
| 6,930,186 | B2 | 8/2005 | Niddam et al. |
| 6,932,983 | B1 | 8/2005 | Straub et al. |
| 6,956,121 | B2 | 10/2005 | Pilarski et al. |
| 7,005,138 | B2 | 2/2006 | Mahashabde et al. |
| 7,029,658 | B2 | 4/2006 | Rabinowitz et al. |
| 7,060,254 | B2 | 6/2006 | Rabinowitz et al. |
| 7,090,830 | B2 | 8/2006 | Hale et al. |
| 7,138,137 | B2 | 11/2006 | Cohen et al. |
| 7,138,523 | B2 | 11/2006 | Rey et al. |
| 7,229,640 | B2 | 6/2007 | Leonard et al. |
| 2001/0024658 | A1* | 9/2001 | Chen et al. ............ 424/452 |
| 2002/0028242 | A1* | 3/2002 | Leonard et al. ........ 424/482 |
| 2004/0213847 | A1* | 10/2004 | Matharu et al. ........ 424/471 |

OTHER PUBLICATIONS

Avalon 2007. Delivering Pharmaceutical Performance. Apr.*

Kaniwa et al., "The Bioavailabilities of Aspirin from an Aspirin Aluminum and an Aspirin Tablets and the Effects of Food and Aluminum Hydroxide Gel," *J. Pharm. Dyn.*, 4, pp. 860-864 (1981).

Rohrs BR et al.; "USP Dissolution Apparatus 3 (Reciprocating Cylinder): Instrument Paramater Effects on Drug Release From Sustained Release Formulations", *J Pharm Sci.* Aug. 1995, 84(8): 922-6.

Yu, Lawrence X., et al.; "Evaluation of USP Apparatus 3 for Dissolution Testing of Immediate-Release Products"; *AAPS PharmSci* 2002; 4(1); Published Jan. 11, 2002.

Logan Instruments Corp. [Online] [Retrieved Jul. 6, 2007]. Retrieved from the Internet: <URL:http://www.loganinstruments.com/autosystem3000.html> (dated Jul. 6, 2007) 2 pages.

Selective Serotonin Reuptake Inhibitor [Online] [Retrieved Jul. 6, 2007]. Retrieved from the Internet: <URL:http://en.wikipedia.org/wiki/Selective_serotonin_reuptake_inhibitor> (dated Jul. 6, 2007) 16 pages.

* cited by examiner

FORMULATION AND METHOD FOR THE RELEASE OF PAROXETINE IN THE LARGE INTESTINE

FIELD OF THE INVENTION

The present invention relates generally to paroxetine formulations for treating disorders, and in particular to a controlled release formulation which releases paroxetine in the large intestine.

Paroxetine, a serotonin reuptake inhibitor, is effective in the treatment of depression. As a reuptake inhibitor, it is believed that paroxetine increases the availability of serotonin in the synapse by reducing the uptake of serotonin by the serotonin uptake carrier. It is also believed that dysfunction of the serotonin neurons resulting from excessive uptake results in depression, as well as other pathologies of the central nervous system. Not only is paroxetine effective in depression, it is also effective in treating numerous other conditions.

U.S. Pat. No. 4,007,196 discloses the compound, (−)-trans-4-(4'-fluorophenyl)-3-(3'4'-methylenedioxyphenoxymethyl) piperidine, and, in Example 2, a process by which it can be prepared. The compound, which is referred to herein by its common name, paroxetine, is described in the patent as an inhibitor of 5-hydroxytryptamine uptake and, therefore, is of use in the treatment of depression. While the primary activity of paroxetine is the inhibition of the reuptake of serotonin, the cascade of monoamine processes in the brain connects serotonin with both norepinephrine and dopamine. Thus, it is believed that increased availability of serotonin results in increased availability of norepinephrine and dopamine as well.

BRIEF SUMMARY OF THE INVENTION

The present invention provides a controlled or delayed release formulation of paroxetine or a pharmaceutically acceptable salt thereof that is formulated to release a substantial portion of the active ingredient (e.g., paroxetine) in the large intestine. For example, the controlled release paroxetine formulation may be formulated to release at least substantially the entire active ingredient content from the dosage form during passage through the large intestine. As a result, release of the active ingredient in the stomach and small intestine can be avoided.

In one embodiment, the present invention provides a delayed release paroxetine composition comprising paroxetine or a pharmaceutically acceptable salt thereof, in a controlled release swallow pharmaceutical formulation, that upon administration, releases the paroxetine substantially in the large intestine. For example, in an embodiment of the present invention the controlled release paroxetine formulation may be formulated to release greater than 50% of the paroxetine in the large intestine, such as a release of paroxetine in the large intestine that is greater than about 55%, 60%, 65%, 70%, 75%, 80%, and 90%. In one embodiment, the controlled release paroxetine formulation is formulated to release from about 60 to 75% of the paroxetine in the large intestine.

In another embodiment, the present invention provides a method of treating and/or preventing one or more disorders comprising the steps of administering a therapeutically effective amount of a formulation comprising paroxetine or a pharmaceutically acceptable salt thereof, in a controlled release swallow pharmaceutical formulation to a mammal in need; and releasing at least a substantial portion of the paroxetine in the large intestine of the mammal. In one embodiment, the formulation of the present invention can be used to treat and/or prevent one or more of the following disorders: alcoholism, anxiety, depression, obsessive, compulsive disorder, panic disorder, chronic pain, obesity, senile dementia, migraine, bulimia, anorexia, social phobia, Pre-Menstrual Syndrome (PMS), adolescent depression, trichotillomania dysthymia, major depressive disorders, panic disorders, social anxiety disorders, premenstrual dysphoric disorders, and substance abuse.

Thus, the invention provides a controlled or delayed release formulation that can be used to release a substantial portion of the paroxetine dosage in the large intestine of a patient in need thereof.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements.

In one alternative embodiment, the present invention is directed to a controlled and/or delayed release formulation of paroxetine or a pharmaceutically acceptable salt thereof that is formulated to release a substantial portion of the active ingredient content (e.g., paroxetine) in the large intestine. For example, the controlled release paroxetine formulation may be formulated to release substantially the entire active ingredient from the dosage form during passage through the large intestine. As a result, release of the active ingredient in the stomach and small intestine can be substantially avoided. In one embodiment, the controlled release paroxetine formulation may be formulated to release greater than 50% of the paroxetine in the large intestine, such as a release of paroxetine in the large intestine that is greater than about 55%, 60%, 65%, 70%, 75%, 80%, and 90%. In one embodiment, the controlled release paroxetine formulation is formulated to release from about 60 to 75% of the paroxetine in the large intestine.

Generally, controlled release paroxetine formulations according to the present invention are formulated so that release of the active ingredient substantially occurs in an environment having a pH range from about 5.5 to 8, and in particular from about 6.8 to 8. In an embodiment, the delayed and/or controlled release paroxetine formulation is formulated for substantial release of the active ingredient at a pH of about 6.8 or greater.

In some embodiments, the controlled release paroxetine formulation can be formulated so that the release of the active ingredient generally occurs from about 5 to 12 hours post ingestion, and in particular from about 7 to 10 hours post ingestion. In one embodiment, controlled release formulations of paroxetine may be formulated to have a delayed release so that significant release of the paroxetine active ingredient occurs about 4 to 5 hours after oral ingestion of the dosage form. For example, in one embodiment, about 5 to 10% of the dosage form has been released after about 5 hours following ingestion. In particular, about 20 and 40% of the dosage form has been released by about 7 hours following ingestion, and about 50 to 80% of the dosage form has been released by about 10 hours following oral ingestion.

By controlled release is meant any formulation technique wherein release of the active substance from the dosage from is modified to occur at a slower rater than that from an immediate release product, such as a conventional swallow tablet or capsule.

By delayed release is meant any formulation technique wherein release of the active substance from the dosage form is modified to occur at a later time than that from a conventional immediate release product. In one embodiment, the present invention provides both a controlled and delayed formulation.

Generally, the active ingredient of the present formulations includes paroxetine and pharmaceutically acceptable salts thereof. Examples of pharmaceutically acceptable salts of paroxetine include, but are not limited to, paroxetine hydrochloride, paroxetine hydrobromide, paroxetine acetate and paroxetine maleate. In one embodiment, the salt is crystalline paroxetine hydrochloride hemi-hydrate. In one embodiment, paroxetine used in the present invention is suitably in the form of the free base or a pharmaceutically acceptable salt thereof. In another embodiment, paroxetine may be in the form of the hydrochloride hemihydrate. Paroxetine hydrochloride hemihydrate may be prepared according to the procedures generally outlined in U.S. Pat. No. 4,721,723.

Solid medicaments comprising the controlled release paroxetine formulation of the present invention may be obtained by conventional methods of blending, filling, tableting or the like. Repeated blending operations may be used to distribute paroxetine or a salt thereof throughout those medicaments employing large quantities of fillers. When the medicament is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in pharmaceutical practice. The medicament may also be in the form of an ingestible capsule, for example of gelatin containing paroxetine or a salt thereof if desired with a carrier or other excipients.

Enteric formulations are often used to protect the active ingredient from the strongly acid contents of the stomach. Such formulations are created by coating a solid dosage form with a film of a polymer which is insoluble in acid environments, and soluble in basic environments. Exemplary films are cellulose acetate phthalate, polyvinyl acetate phthalate, hydroxypropyl methylcellulose phthalate and hydroxypropyl methylcellulose acetate succinate. In one embodiment, pH-sensitive polymers may be chosen to bypass release in the stomach and small intestine to deliver sustained/controlled levels in the large intestine. As discussed above, the controlled and delayed release of the paroxetine formulation allows a substantial portion of the active ingredient to be released in the large intestine.

In terms of the polymeric coating agents for covering the surfaces of solid particles pharmaceutically usable polymeric substances can be employed, such as EUDRAGIT RETARD® (copolymer of ethyl methacrylate and trimethylacrylethylammonium chloride, Rohm Pharma Co., Ltd.), EUDRAGIT L® (copolymer of methyl methacrylate and methacrylate, Rohm Pharma Co., Ltd.), EUDRAGIT S® (copolymer of methyl methacrylate and methacrylate, Rohm Pharma Co., Ltd.) as an acrylate polymer, ETHOCEL® (ethylcellulose, Dow Chemical Co., Ltd.), METOLOSE ® (methylcellulose, Shinetsu Kagaku Co., Ltd.), HPMCP® (hydroxypropylmethylcellulose phthalate, Shinetsu Kagaku Co., Ltd.), and (hydroxypropylmethylcellulose acetate succinate, Shinetsu Kagaku Co., Ltd.) as a cellulose derivative, and the mixtures thereof.

The active ingredient particles, granulates, pellet grains or tablets may be coated with a variety of different substances. Suitable coating substances include, but are not limited to, the following, or mixtures of the following substances: hydroxypropylmethyl cellulose phthalate- or acetate succinate; cellulose-, starch-, as well as polyvinyl acetate phthalate; carboxymethyl cellulose; polyvinyl acetate; methylcellulose phthalate, methylcellulose succinate, methyl cellulose phthalate succinate as well as methyl cellulose phthalic acid half ester; zein; ethyl cellulose as well as ethyl cellulose succinate; shellac; gluten; ethylcarboxyethyl cellulose; ethacrylate-maleic acid anhydride copolymer; maleic acid anhydride vinyl methyl ether copolymer; styrol maleic acid copolymerizate; 2-ethylhexylacrylate maleic acid anhydride; crotonic acid vinyl acetate copolymer; glutaminic acid/glutaminic acid ester copolymer; carboxymethylethyl cellulose glycerin mono-octanoate; cellulose acetate succinate; polyarginin; fats, oils, waxes, fatty alcohols; anionic polymerizates of methacrylic acid and methacrylic acid esters (EUDRAGIT®L, EUDRAGIT®S); copolymerizates of acrylic and methacrylic acid esters with a low ammonium group (EUDRAGIT®RS) content, as well as copolymers of acrylic and methacrylic acid esters and trimethyl ammonium methacrylate (EUDRAGIT®RL), copolymerizates of acrylic acid ethyl- and methacrylic acid methyl esters 70:30 (EUDRAGIT®NE 30 D), copolymerizates of acrylic acid, methacrylic acid as well as their esters (ratio of the free carboxyl groups to the ester groups for example 1:1) (EUDRAGIT®L 30 D). In one particular embodiment, the active ingredient core may be coated with a methacrylic acid copolymer Type C (EUDRAGIT® L30D).

In some embodiments, controlled release paroxetine formulations in accordance with the present invention may also contain conventional softeners (e.g. dibutyl sebacate, citric and tartaric acid esters, glycerin and glycerin esters, phthalic acid esters and similar substances). It also is possible to add water-soluble substances such as polyethylene glycols, polyvinylpyrrolidone, copolymerizates of polyvinylpyrrolidone and polyvinyl acetate, hydroxypropyl cellulose, hydroxypropylmethyl cellulose. The addition of solids such as talcum and/or magnesium stearate to the coating is also possible.

Organic acids (such as for example citric acid, tartaric acid, maleic, fumaric, ascorbic acid) may also be incorporated into the pellet grains, granulate grains or tablets.

Polymer materials which swell on contact with aqueous liquids, such as insoluble polymers may be used including crosslinked sodium carboxymethylcellulose, crosslinked hydroxypropylcellulose, high molecular weight hydroxypropylmethylcellulose, carboxymethyl starch, potassium methacrylate/divinylbenzene copolymer, polymethylmethacrylate, crosslinked polyvinylpyrrolidone, high molecular weight polyvinylalcohols etc. Gellable polymer materials include methylcellulose, carboxymethylcellulose, low molecular weight hydroxypropylmethylcellulose, low molecular weight polyvinylalcohols, polyethylene glycols, non-crosslinked polyvinylpyrrolidone. Polymers possessing both swelling and gelling properties such as medium viscosity hydroxypropylmethylcellulose and medium viscosity polyvinylalcohols can also be used. Adjuvant substances may include mannitol, ethylcellulose, magnesium stearate, colloidal silica and others.

In a further embodiment, the present invention provides a system for the controlled release of an active ingredient which is an SSRI such as paroxetine, comprising (a) a deposit-core comprising a therapeutically effective amount of the active ingredient, and (b) a support-platform applied to the deposit-core, wherein the deposit-core contains at least the active ingredient, and at least one member selected from the group consisting of (1) a polymeric material which swells on contact with water or aqueous liquids and a gellable polymeric material wherein the ratio of the swellable polymeric material to the gellable polymeric material is in the range 1:9 to 9:1, and (2) a single polymeric material having both swelling and gelling properties, and wherein the support-platform is an elastic support, applied to the deposit-core so that it partially covers the surface of the deposit-core and follows changes due to hydration of the deposit-core and is slowly soluble and/or slowly gellable in aqueous fluids. The support-platform may comprise polymers such as hydroxypropylmethylcellulose, plasticizers such as a glyceride, binders such as polyvinylpyrrolidone, hydrophilic agents such as lactose and silica, and/or hydrophobic agents such as magnesium stearate and glycerides. In one embodiment, the polymer(s) may comprise up 30 to 90% by weight of the support-platform, for example about 35 to 40%. Plasticizer may make up at least 2% by weight of the support-platform, for example about 15 to 20%. Binder(s), hydrophilic agent(s) and hydrophobic agent(s) may total up to about 50% by weight of the support-platform, for example about 40 to 50%.

Coating may be effected by spraying solutions of the foregoing substances in organic or aqueous solvents or suspensions of those substances in organic solvents or water. It also is possible to add further auxiliary substances to optimize their processability, such as for example surface-active substances and pigments. The spraying may be effected for example in a coating drum or in perforated drums or in an air suspension process (for example Glatt WLSD5 fluidized air bed installation). Coating may also take place using a coacervation process in which so-called microcapsules are formed. Coating may also be effected by coagulation of aqueous dispersions of the previously mentioned substances by mixing the active substance with the dispersion and removing the water by drying. Coated active ingredients particles and coated granulates may be pressed into tablets, coated pellets may be filled into hard gelatin capsules.

In certain instances, coating the particles or granulates containing the active ingredient may require more coating substance used in the case of pellets since the surface of the particles or granules is larger than that of pellets.

In other embodiments, the controlled release paroxetine formulation can be prepared by admixture of paroxetine or salt thereof with an appropriate carrier, which may contain a diluent, binder, filler, disintegrant, flavouring agent, colouring agent, lubricant or preservative in conventional manner.

In one alternative embodiment, the present invention provides a controlled release paroxetine composition comprising a core that contains a combination of paroxetine or a pharmaceutically acceptable salt thereof and a pharmaceutically acceptable carrier. The composition can also include an outer enteric coating that at least substantially envelopes and encases the core. To help provide the desired controlled release, the outer enteric coating comprises a pH sensitive polymer that is substantially insoluble in acid environments (e.g., at a pH of less than 6.8) and is soluble at a pH of 6.8 or greater. In one embodiment, the pH sensitive polymer is selected so that the active ingredient of the core is substantially released during passage through the large intestine.

In a further embodiment, the present invention provides a controlled release paroxetine composition comprising a core containing a combination of paroxetine hydrochloride hemihydrate; microcrystallines cellulose; magnesium stearate; colloidal silicon dioxide; hypromellose; hydroxypropyl cellulose; and lactose monohydrate. In one embodiment, the composition includes an outer enteric coating comprising methacrylic acid copolymer that substantially envelopes the core.

Controlled release paroxetine formulations in accordance with the present invention may be administered orally in caplet, tablet, particle, granule, or powder forms. The dosage administered will, of course, vary depending on the use and known factors such as the pharmacodynamic characteristics of the active ingredient; age, health, and weight of the recipient; nature and extent of symptoms, kind of concurrent treatment, frequency of treatment, and the effect desired. The recipient may be any type of mammal, but is preferably a human.

In one embodiment, dosage forms (compositions) of the controlled release paroxetine formulation may contain about 1 milligram to 100 milligrams of active ingredient per unit, and in particular, from about 10 to 80 milligrams of active ingredient per unit, such as from about 14 to 75 milligrams, 20 to 70 milligrams, 35 to 65 milligrams, 40 to 50 milligrams, or from about 40 to 45 milligrams of active ingredient per unit. In one embodiment, a unit dose of paroxetine will generally contain from 20 to 1000 mg and preferably will contain from 30 to 500 mg, in particular 50, 100, 150, 200, 250, 300, 350, 400, 450, or 500 mg. The composition may be administered once or more times a day for example 2, 3 or 4 times daily, and the total daily dose for a 70 kg adult will normally be in the range 100 to 3000 mg. Alternatively the unit dose may contain from 2 to 20 mg of paroxetine and be administered in multiples, if desired, to give the preceding daily dose. In these pharmaceutical compositions, the active ingredient will ordinarily be present in an amount of about 0.5-95% by weight based on the total weight of the composition.

For use in the treatment of targeted disorders, by way of general guidance, a daily oral dosage of the active ingredient can generally range from about 0.001 to 1000 mg/kg of body weight.

For instance, for oral administration in the form of a tablet or capsule, the active ingredient can be combined with an oral, non-toxic, pharmaceutically acceptable, inert carrier, including but not limited to, lactose, starch, sucrose, glucose, methyl cellulose, magnesium stearate, dicalcium phosphate, calcium sulfate, mannitol, sorbitol and the like. Additionally, when desired or necessary, suitable binders, lubricants, disintegrating agents, and coloring agents can also be incorporated into the mixture. Suitable binders may include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms may include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

In some embodiments, the controlled release paroxetine formulations of the present invention may also be coupled with soluble polymers as targetable drug carriers. Such polymers can include, for example, polyvinylpyrrolidone, pyran copolymer, polyhydroxypropylmethacrylamide-phenol, polyhydroxyethylaspartamidephenol, or polyethyleneoxide-polylysine substituted with palmitoyl residues. In one embodiment, the controlled release paroxetine formulations of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

In one embodiment, the paroxetine formulation of the present invention can be used to treat and/or prevent one or more of the following disorders: alcoholism, anxiety, depression, obsessive, compulsive disorder, panic disorder, chronic pain, obesity, senile dementia, migraine, bulimia, anorexia, social phobia, Pre-Menstrual Syndrome (PMS), adolescent depression, trichotillomania dysthymia, major depressive disorders, panic disorders, social anxiety disorders, premenstrual dysphoric disorders and substance abuse.

The present invention provides a method of treating and/or preventing one or more disorders by administering a therapeutically effective amount and/or a prophylactic amount of a controlled release or delayed release formulation containing paroxetine or a pharmaceutically acceptable salt thereof, to a sufferer in need thereof. By "therapeutically effective amount" it is meant an amount of the active ingredient (e.g., paroxetine or a pharmaceutically acceptable salt thereof) to a mammal is effective to treat and/or prevent one or more targeted disorders.

The following examples are provided for the purpose of illustration only and should not be construed as limiting the invention in any way.

EXAMPLES

Example 1

Two controlled release paroxetine formulations (12.5 mg and 25 mg) were prepared and are summarized in Table 1 below. The formulations (12.5 and 25 mg) were used in a series of tests to simulate certain conditions in the stomach, small intestine, and large intestine. The results of the tests are summarized in FIGS. 1 to 4 and are specifically discussed below.

TABLE 1

Formulation Data for 12.5 and 25 mg controlled release Paroxetine

| Ingredient | Amount (mg)/Tablet | | Amount (%) Tablet | |
|---|---|---|---|---|
| | 12.5 mg | 25 mg | 12.5 mg | 25 mg |
| Cores | | | | |
| Paroxetine Hydrochloride Hemihydrate, USP | 14.22[1] | 28.45[2] | 6.45 | 12.91 |
| Lactose Monohydrate, NF (FAST FLO ®) | 68.8 | 60.0 | 31.22 | 27.22 |
| Microcyrstalline Cellulose, NF (AVICEL ® PH 102) | 42.78 | 37.25 | 19.41 | 16.90 |
| Hypromellose, USP (K100 Premium LVCR) | 60.0 | 60.0 | 27.22 | 27.22 |
| Hydroxypropyl Cellulose, NF (KLUCEL ® EXF) | 12.0 | 12.0 | 5.44 | 5.44 |
| Magnesium Stearate, NF | 1.8 | 1.8 | 0.82 | 0.82 |
| Colloidal Silicon Dioxide, NF (CAB-O-SIL ® M-5) | 0.4 | 0.4 | 0.18 | 0.18 |
| D&C Red #30 Lake HT (26-34%) | — | 0.1 | — | 0.05 |
| Enteric Coating | | | | |
| Methacrylic Acid Copolymer NF, Type C (EUDRAGIT ® L30D) | 9.00 | 9.00 | 4.08 | 4.08 |
| Talc, USP, Micronized (Alphafil 500) | 1.50 | 1.50 | 0.68 | 0.68 |
| Teiethyl Citrate, NF (TEC-PG) | 1.35 | 1.35 | 0.61 | 0.61 |
| Polysorbate 80 NF | 0.12 | 0.12 | 0.05 | 0.05 |
| Sodium Hydroxide, NF | 0.03 | 0.03 | 0.01 | 0.01 |
| Film Coating | | | | |
| White Opadry II (Y-22-7719) Solids | 8.0 | — | 3.63 | — |
| Lavender Opadry II (Y-22-19264) Solids | — | 8.0 | — | 3.63 |
| Clear Opadry (YS-1-7006) Solids | 0.4 | 0.4 | 0.18 | 0.18 |
| Total | 220.4 | 220.4 | 100 | 100 |

[1]Equivalent to 12.5 mg of Paroxetine
[2]Equivalent to 25 mg of Paroxetine

Figure 1:
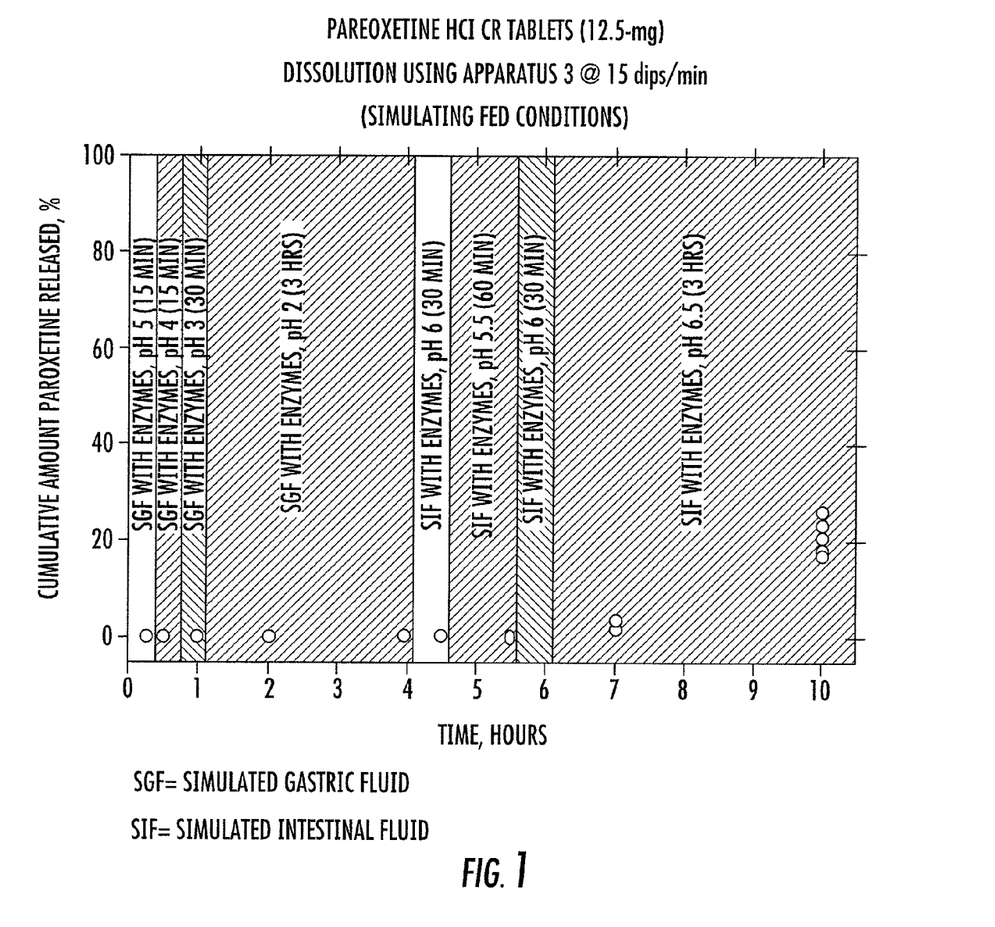
FIG. 1 illustrates the simulated dissolution of 12.5 mg Paroxetine HCl CR tablets in the fed state.
Figure 2:
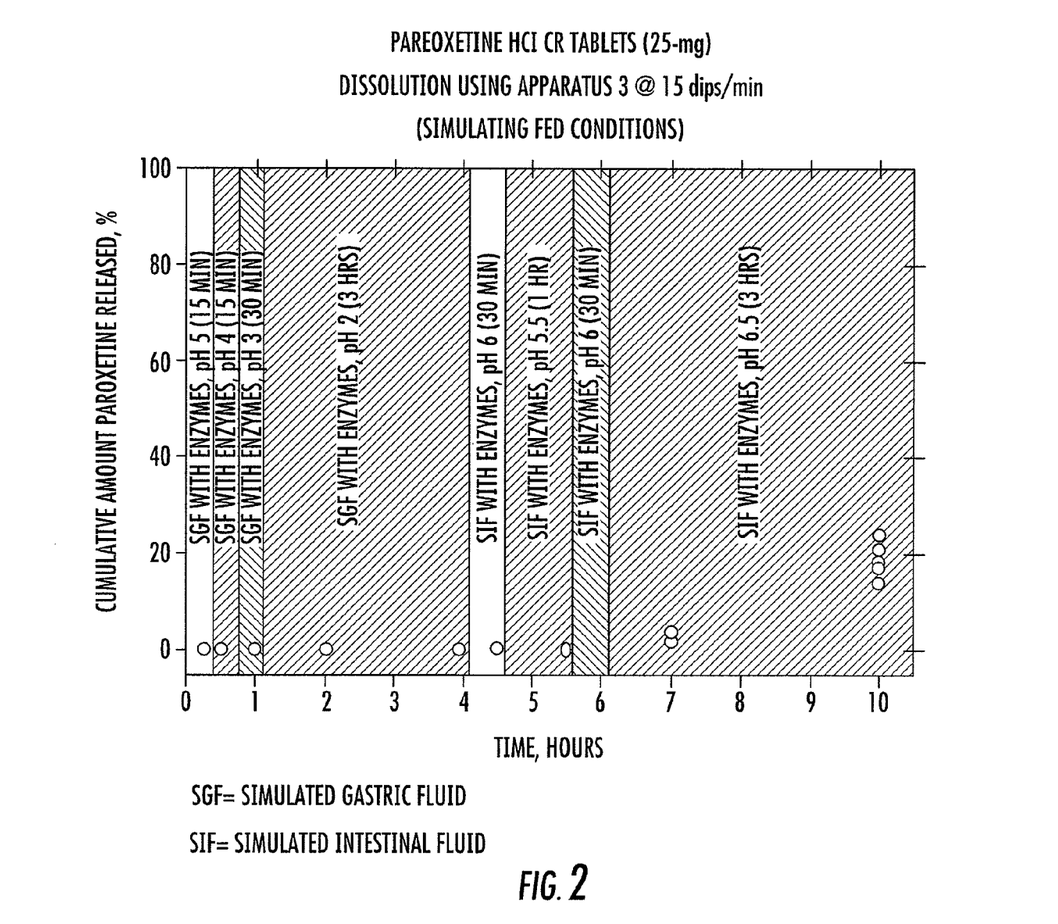
FIG. 2 illustrates the simulated dissolution of 25 mg Paroxetine HCl CR tablets in the fed state.
Figure 3:
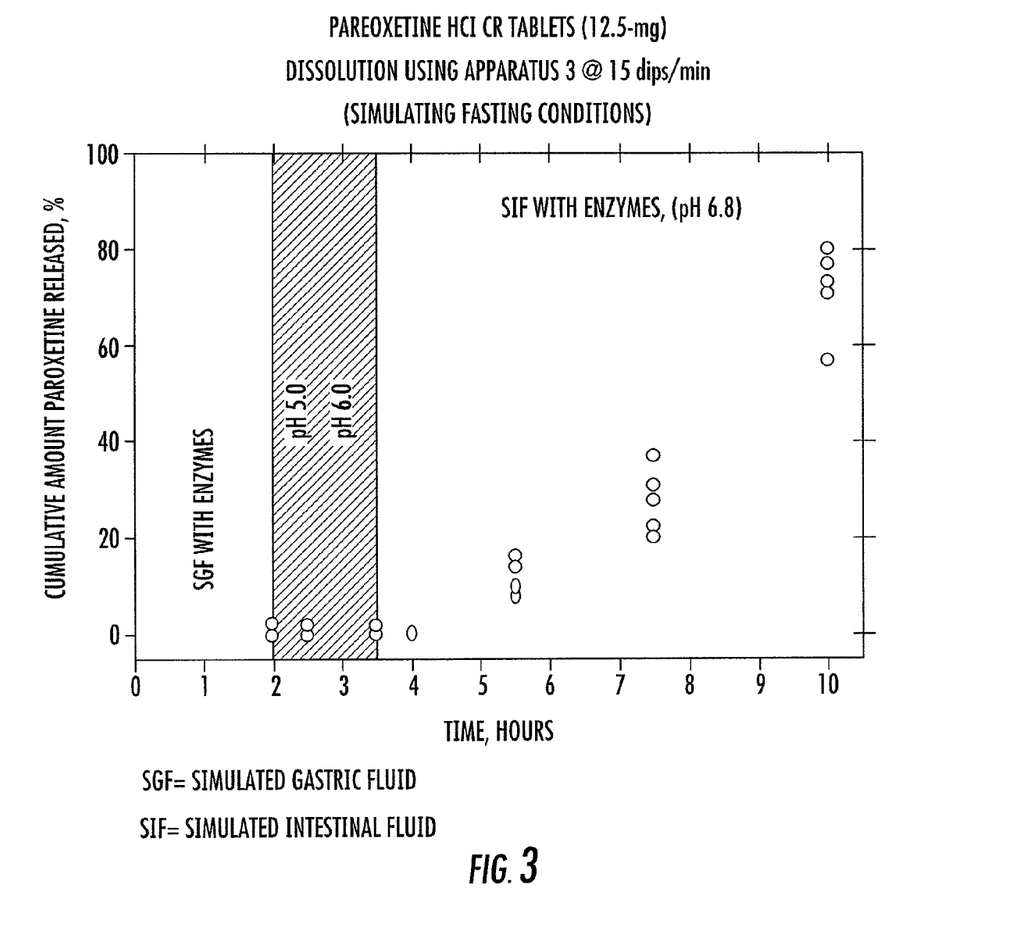
FIG. 3 illustrates the simulated dissolution of 12.5 mg Paroxetine HCl CR tablets in the fasting state.
Figure 4:
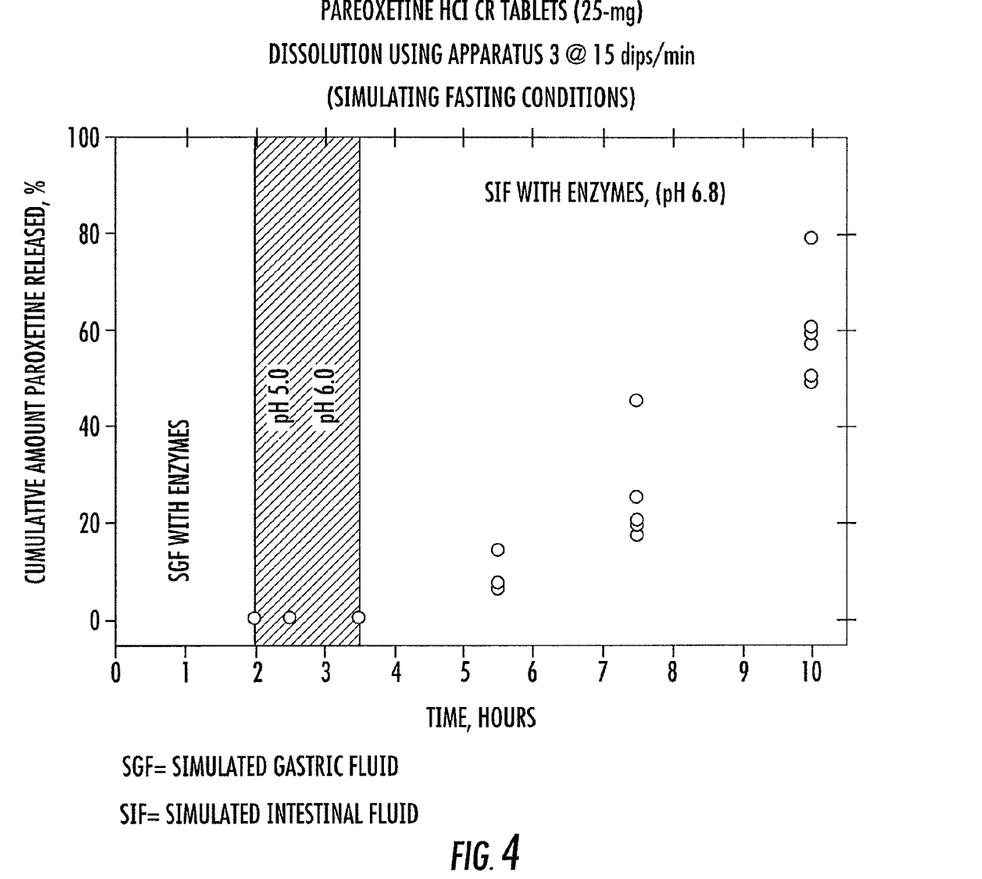
FIG. 4 illustrates the simulated dissolution of 25 mg Paroxetine HCl CR tablets in the fasting state.

The 12.5 mg and 25 mg formulations were tested under conditions that simulated certain conditions in the stomach, small intestines and large intestine. The testing and simulated conditions were performed according to USP 29-NF 24 using Apparatus 3 at a rate of 15 dips/min. The pH condition for each time period is labeled in each chart. In each of the FIGS. the portion of the chart represented by SGF simulates conditions in the stomach; the shaded area of the chart simulates certain physiological conditions that may be encountered in the small intestine; and the area to the right of the shade area (SIF) simulates certain conditions of the large intestine. FIGS. 1 and 2 simulate fed conditions, whereas FIGS. 3 and 4 simulate fasting conditions.

Generally, it has been reported that it will take about 3 to 4 hours for an ingested substance to pass through the stomach and small intestine, and into the large intestine. As can be seen in FIGS. 1 to 4, controlled release paroxetine formulations in accordance with the present invention can be formulated so that substantially the entire dosage form of the active ingredient is released in the large intestine. For example, FIGS. 1 and 2, which are simulated under fed conditions and are directed to dosage forms of 12.5 mg and 25 mg paroxetine, respectively, show that the formulations have a delayed release of a substantial amount of paroxetine until after about 7 hours following ingestion. Further, FIGS. 3 and 4, which are simulated under fasting conditions and are directed to dosage forms of 12.5 mg and 25 mg paroxetine, respectively, show that after about 5 hours following ingestion about 10% to 20% of the paroxetine has been released, and that after about 7 hours following ingestion about 20% to 40% of the paroxetine has been released, and finally after about 10 hours following ingestion 60% to 85% of the paroxetine has been released.

From these examples, it can be seen that the present invention provides a formulation and associated method for the controlled and/or delayed release of paroxetine in the large intestine. As a result, significant release of paroxetine in the stomach or small intestine can be avoided. Accordingly, the present invention provides a pharmaceutical composition for use in the treatment and/or prevention of disorders which comprises a controlled release and/or delayed release formulation that contains paroxetine or a pharmaceutically acceptable salt thereof.

Example 2

In Example 2, a controlled release paroxetine formulation that contained 37.5 mg of paroxetine HCL was prepared in tablet form. Table 2 summarizes an exemplary composition of the tablet formulation. Table 5 includes exemplary properties of the formulation of Table 2. Table 3 summarizes an exemplary composition for an enteric coating that is in accordance with one alternative embodiment of the present invention. Table 4 includes an exemplary composition for the composition of the core containing the active ingredient that is in accordance with one embodiment of the present invention.

TABLE 2

Formulation of Paroxetine HCl ER Tablets, 37.5 mg

| Batch Formula Ingredients | mg per unit |
|---|---|
| Part I | |
| Paroxetine HCl Hemihydrate | 42.67 |
| Colloidal Silicon Dioxide, NF (CAB-O-SIL ®, M5) | 0.40 |
| Magnesium Stearate | 0.60 |
| Part II | |
| Hydroxypropyl Cellulose (EXF) | 12.0 |
| Hypromellose 2208 (METHOCEL ® K100LVCR) | 44.0 |
| Lactose, FAST FLO ® | 76.0 |
| Microcrystalline Cellulose, AVICEL ® PH102 | 22.33 |
| Part III | |
| D&C Red #30 (Lake HT 26-34%) | 0.02 |
| FD&C Yellow #6 (15%-18%) | 0.18 |
| Colloidal Silicon Dioxide, NF (CAB-O-SIL ®, M5) | 0.20 |
| Magnesium Stearate | 1.60 |
| Core Tablets Total | 200.0 |
| Part IV | |
| Enteric Coating Suspension for Paroxetine Hydrochloride Extended-release Tablets | (60.0) |
| Solid Contribution from Enteric Coating Suspension for Paroxetine Hydrochloride Extended-release Tablets | 12.0 |
| Enteric Coated Tablets Total | 212.0 |
| Part V | |
| Orange Opadry II (Y-24-9708) 20% w/w Coating Suspension | (40.0) |
| Solid Contribution from Orange Opadry II (Y-24-9708) 20% w/w Coating Suspension | 8.0 |
| Part VI | |
| Clear Aqueous Film-Coating Solution (Clear YS-1-7006) | (6.98) |
| Solid Contribution from Clear Aqueous Film-Coating Solution (Clear YS-1-7006) | 0.4 |
| Film Coated Tablets Total | 220.4 |

TABLE 3

Formulations of Paroxetine HCl ER Tablets, 37.5 mg

| Batch Formula Ingredients | mg per unit |
|---|---|
| Part IV | |
| Methacrylic Acid Copolymer Type C (EUDRAGIT ® L30D) | (30.0) |
| Solids Contribution from Methacrylic Acid Copolymer Type C (EUDRAGIT ® L30D) | 9.0 |
| Talc, Micronized (Alphafil 500) | 1.50 |
| Triethyl Citrate (TEC-PG) | 1.35 |
| Polysorbate 80, NF | 0.12 |
| Sodium Hydroxide, NF | 0.030 |
| Purified Water, USP | (27.0) |
| Total Suspension | (60.0) |
| Total Solid Contribution from the Suspension | 12.0 |

TABLE 4

Compositions of Paroxetine HCl ER Tablets, 37.5 mg

| Batch Formula Ingredients | mg per unit |
|---|---|
| Paroxetine HCl Hemihydrate | 42.67 |
| Hydroxypropyl Cellulose (EXF) | 12.0 |
| Hypromellose 2208 (METHOCEL ® K100LVCR) | 44.0 |
| Lactose, FAST FLO ® | 76.0 |
| Microcrystalline Cellulose, AVICEL ® PH102 | 22.33 |
| D&C Red #30 (Lake HT 26-34%) | 0.02 |
| FD&C Yellow #6 (15%-18%) | 0.18 |
| Colloidal Silicon Dioxide, NF (CAB-O-SIL ®, M5) | 0.60 |
| Magnesium Stearate | 2.20 |
| Core Tablets Total | 200.0 |
| Methacrylic Acid Copolymer Type C (EUDRAGIT ® L30D) (Solid Content) | 9.0 |
| Talc, Micronized (Alphafil 500) | 1.50 |
| Triethyl Citrate (TEC-PG) | 1.35 |
| Polysorbate 80, NF | 0.12 |
| Sodium Hydroxide, NF | 0.030 |
| Enteric Coated Tablets Total | 212.0 |
| Orange Opadry II (Y-24-9708) 20% w/w Coating Suspension | 8.0 |
| Clear Aqueous Film-Coating Solution (Clear YS-1-7006) | 0.4 |
| Film Coated Tablets Total | 220.4 |

Example 3

Embodiments of the Present Invention can be Prepared as Follows

1. Initial Blending/Compacting/Milling
   1.1. Add Part I Cab-O-Sil and Part I Magnesium Stearate to a V-blender and blend for three (3) minutes, discharge, and pass through a #30 mesh screen.
   1.2. Add Part I Paroxetine HCl hemihydrate and screened lubricant pre-blend to the same V-blender and mix for fifteen (15) minutes (do not discharge).

1.3. Add Part II Microcrystalline Cellulose (Avicel PH102), Part II Hydroxypropyl Cellulose (Klucel EXF), Part II Hydroxypropyl methylcellulose (HPMC K100 LV), and Part II Lactose, Fast Flo to the same V-blender and blend for fifteen (15) minutes.

1.4. Compact the blended material using a Chilsonator Compactor.

1.5. Pass compacted material through a Fitzmill using the following parameters: #1B screen, knives forward, medium speed.

2. Blending/Compressing 2.1. Add Part III Colloidal Silicon Dioxide, Part III D&C Red #30 (Lake HT 26-34%), Part III FD&C Yellow #6 (Lake HT 15-18%) and Part III Magnesium Stearate to a V-blender and blend for three (3) minutes, discharge, and pass through a #30 mesh screen.

2.2. Add approximately half of the milled material, the screened Part III lubricant pre-blend, and the remaining milled material to the same V-blender and blend for fifteen (15) minutes.

2.3. Compress the final blend into tablets using a rotary tablet press.

3. Enteric Coating/Film Coating 3.1. Apply Enteric Coating Suspension (prepared based on separate batch ticket) for Paroxetine HCl Extended-release tablets to the core tablets using a perforated coating pan to target weight gain.

3.2. Apply Opadry II Coating Suspension (prepared based on separate batch ticket) to the enteric coated tablet using a perforated coating pan to target weight gain.

3.3. Apply the specified quantity of Clear Aqueous Film Coating Solution (prepared based on separate batch ticket) to the color coated tablets using a perforated coating pan.

TABLE 5

Physical Testing Results of Paroxetine HCl ER Tablets, 37.5 mg, Optimization Batch

| Blend | Initial Blend | Final Blend |
|---|---|---|
| Bulk Density (g/mL) | | |
| Poured Bulk Density: | 0.46 g/mL | 0.51 g/mL |
| Tapped Bulk Density (200x): | 0.70 g/mL | 0.75 g/mL |
| Mesh Analysis (%) | | |
| # 20 | 0.0 | 0.0 |
| # 40 | 0.0 | 5.7 |
| # 60 | 1.6 | 11.4 |
| # 80 | 6.6 | 10.6 |
| # 100 | 8.6 | 7.7 |
| # 140 | 21.3 | 14.6 |
| Pan | 61.9 | 50.0 |
| Moisture | | |
| LOD (%) | 2.02 | 1.84% |

| Tablets | Core Tablets |
|---|---|
| Tablet Weight | |
| Average (mg) (Range): | 200 mg (190-210 mg) |
| RSD (%): | 1.21% RSD |
| Hardness (kp) | |
| Average: | 8.6 kp |
| Hardness Trial Range: | 4.5-13.0 kp |
| Thickness (inch) | |
| Average: | 0.156" |
| Hardness Trial Range: | 0.165-0.150" |

TABLE 5-continued

Physical Testing Results of Paroxetine HCl ER Tablets, 37.5 mg, Optimization Batch

| Friability (%) | |
|---|---|
| At Target Hardness: | 0.0% |
| Hardness Trial Range: | 0.0-0.1% |
| Disintegration Time (min) | |
| Average: | N/A |
| Hardness Trial Range: | N/A |

Many modifications and other embodiments of the invention set forth herein will come to mind to one skilled in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A formulation comprising paroxetine or a pharmaceutically acceptable salt thereof, in a controlled or delayed release swallow pharmaceutical formulation, and an enteric coating surrounding the core wherein the enteric coating consists of about 75% by weight methacrylic acid copolymer, about 12.5% by weight talc, about 11.25% by weight softener, about 1% by weight polysorbate, and about 0.25% by weight sodium hydroxide, wherein after about 5 to about 12 hours post administration, releases more than 65% of the paroxetine or a pharmaceutically acceptable salt thereof in a large intestine of a mammal, and is substantially insoluble in a stomach and a small intestine of the mammal.

2. The formulation of claim 1, wherein the formulation releases more than 70% of the paroxetine or a pharmaceutically acceptable salt thereof in the large intestine.

3. The formulation of claim 1, wherein a substantial portion of the paroxetine or a pharmaceutically acceptable salt thereof is released after at least about 5 hours following administration.

4. The formulation of claim 1, wherein a substantial portion of the paroxetine or pharmaceutically acceptable salt thereof is released after at least about 7 hours following administration.

5. The formulation of claim 1, wherein less than 35% of the paroxetine or pharmaceutically acceptable salt thereof is released in the stomach, small intestine, or a combination thereof.

6. The formulation of claim 1, wherein the formulation comprises a caplet, tablet, particle, granule, or powder form.

7. A method of treating or preventing any one or more of alcoholism, anxiety, depression, obsessive compulsive disorder, panic disorder, chronic pain, obesity, senile dementia, migraine, bulimia, anorexia, social phobia, Pre-Menstrual Syndrome (PMS), adolescent depression, major depressive disorders, panic disorders, social anxiety disorders, premenstrual dysphoric disorders, and substance abuse comprising administering a therapeutically effective amount of the formulation of claim 1.

8. The formulation of claim 1, wherein the formulation is a controlled and delayed release formulation.

9. A formulation comprising paroxetine or a pharmaceutically acceptable salt thereof, in a delayed release swallow pharmaceutical formulation, and an enteric coating wherein the enteric coating consists of about 75% by weight methacrylic acid copolymer, about 12.5% by weight talc, about 11.25% by weight softener, about 1% by weight polysorbate, and about 0.25% by weight sodium hydroxide.

10. A method of treating and/or prophylaxis of one or more psychiatric disorders comprising the steps of:
   administering a therapeutically effective amount of the formulation of claim 1 to a mammal in need thereof.

11. The method of claim 10, wherein the amount of paroxetine or a pharmaceutically acceptable salt thereof in the formulation is between 1 and 100 mgs per unit.

12. The method of claim 10, further comprising the step of administering the formulation to a mammal in order to treat one or more of the following disorders: alcoholism, anxiety, depression, obsessive, compulsive disorder, panic disorder, chronic pain, obesity, senile dementia, migraine, bulimia, anorexia, social phobia, Pre-Menstrual Syndrome (PMS), adolescent depression, trichotillomania dysthymia, major depressive disorders, panic disorders, social anxiety disorders, premenstrual dysphoric disorders and substance abuse.

13. The method of claim 10, wherein about greater than 65% of the paroxetine or a pharmaceutically acceptable salt thereof is released after about 5 hours following ingestion.

14. The method of claim 10, wherein about 70% or more of the paroxetine or a pharmaceutically acceptable salt thereof released after about 5 hours following ingestion.

15. A delayed release paroxetine composition comprising:
   a core containing paroxetine or a pharmaceutically acceptable salt thereof, and a pharmaceutically acceptable carrier; and
   an enteric coating surrounding the core wherein the enteric coating consists of about 75% by weight methacrylic acid copolymer, about 12.5% by weight talc, about 11.25% by weight softener, about 1% by weight polysorbate, and about 0.25% by weight sodium hydroxide.

16. The composition of claim 15, wherein the paroxetine or a pharmaceutically acceptable salt thereof is selected from the group consisting of paroxetine hydrochloride, paroxetine hydrobromide, paroxetine acetate, paroxetine maleate, and paroxetine hydrochloride hemi-hydrate.

17. The composition of claim 15, wherein the carrier comprises one or more of magnesium stearate, starch, glucose, lactose, sucrose, rice flour and chalk.

18. The composition of claim 15, wherein the carrier comprises colloidal silicon dioxide and magnesium stearate.

19. A controlled release paroxetine composition comprising:
   a core comprising
   paroxetine hydrochloride hemihydrate;
   microcrystalline cellulose;
   magnesium stearate;
   colloidal silicon dioxide;
   hypromellose;
   hydroxypropyl cellulose; and
   lactose monohydrate; and
   an enteric coating surrounding the core wherein the enteric coating consists of about 75% by weight methacrylic acid copolymer, about 12.5% by weight talc, about 11.25% by weight softener, about 1% by weight polysorbate, and about 0.25% by weight sodium hydroxide,
   and wherein the methacrylic acid copolymer is chosen such that the composition is soluble at a pH of 6.8 in a large intestine of a mammal and is substantially insoluble in a stomach and a small intestine of the mammal.

20. The formulation of claim 1, wherein the softener comprises at least one of dibutyl sebacate, a citric acid ester, a tartaric acid ester, a glycerin, a glycerin ester, and a phthalic acid ester.

21. The composition of claim 19, wherein the softener comprises triethyl citrate.

* * * * *